United States Patent [19]

Heller et al.

[11] Patent Number: 4,737,449

[45] Date of Patent: Apr. 12, 1988

[54] PHOTOCHROMIC 3-PYRRYL FULGIDES AND FULGIMIDES

[75] Inventors: Harry G. Heller, Cardiff, Wales; Stephen N. Oliver, Felixstowe, England; Stuart A. Harris, Cardiff, Wales

[73] Assignee: The Plessey Company Plc, Essex, England

[21] Appl. No.: 822,071

[22] Filed: Jan. 24, 1986

[30] Foreign Application Priority Data

Jan. 24, 1985 [GB] United Kingdom ............ 8501779

[51] Int. Cl.$^4$ ............... G03C 1/733; C07D 405/06; C07D 409/06
[52] U.S. Cl. ............................. 430/343; 430/342; 430/945; 430/962; 548/517; 548/518
[58] Field of Search .......... 548/517, 518; 430/342, 430/343, 945, 962

[56] References Cited

U.S. PATENT DOCUMENTS 4,220,708  9/1980  Heller .................... 430/19 X

FOREIGN PATENT DOCUMENTS 2532244  2/1976  Fed. Rep. of Germany ...... 548/517

Primary Examiner—Mark L. Berch
Assistant Examiner—William A. Teoli, Jr.
Attorney, Agent, or Firm—Sughrue, Mion, Zinn, Macpeak, and Seas

[57] ABSTRACT

A series of novel 3-pyrryl fulgides and fulgimides are disclosed which are photochromic. The photochromic compounds are coloured by subjecting them to irradiation in the near ultraviolet and will revert to the colourless form on exposure to visible light, especially light having a wavelength in 600 to 650 nm band.

11 Claims, 6 Drawing Sheets

| | | $\lambda_{max}$ nm |
|---|---|---|
| Example 1 | 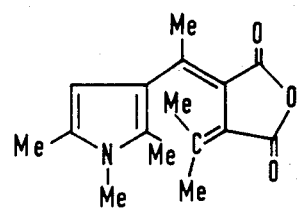 | 632 |
| Example 2 | 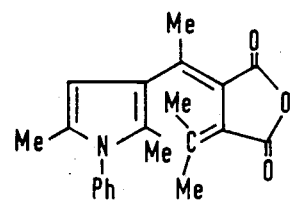 | 610 |
| Example 3 | 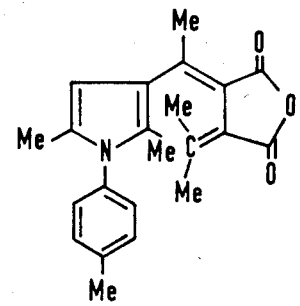 | 615 |
| Example 4 | 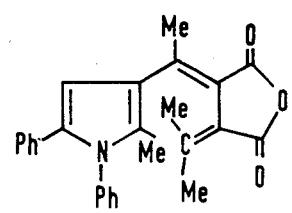 | 605 |
| Example 5 | 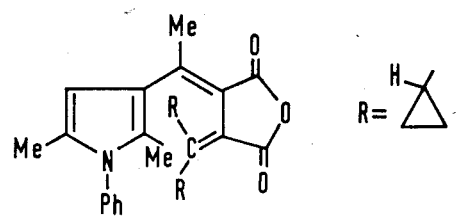 | 635 |

PHOTOCHROMIC 3-PYRRYL FULGIDES AND FULGIMIDES

This invention relates to a series of photochromic heterocyclic fulgides and fulgimides.

BACKGROUND OF THE INVENTION

U.S. Pat. No. 4,220,708 (Heller) describes inter alia a series of 3-furyl and 3-thienyl fulgides and fulgimides having the general formula (I) below:

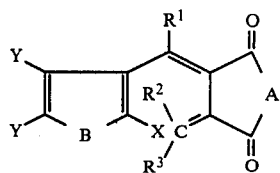

wherein
$R^1$ represents an alkyl, aryl or aralkyl group,
A represents oxygen or >N—$R^6$, in which $R^6$ is alkyl or aryl,
B represents oxygen or sulphur,
$R^2$ and $R^3$ independently represent an alkyl, aryl or aralkyl group or one of $R^2$ and $R^3$ represent hydrogen and the other an alkyl, aryl or aralkyl group. Alternatively,

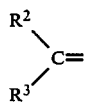

may represent an adamantylidene group,
X represents hydrogen or an alkyl, aryl or aralkyl group and each Y is independently selected from hydrogen, halogen, alkyl, aryl, aralkyl, alkoxy and aryloxy group.

The compounds described in the above U.S. patent exhibit improved photochromic properties compared with previously known photochromic compounds.

In particular they show an increased sensitivity and response due in part to the coloured species absorbing less strongly and acting less as an internal filter at wavelengths used to promote photocolouration.

The colouring process takes place by subjecting the compound to near ultraviolet radiation (eg 366 nm) and photobleaching takes place in the visible spectrum *below* 600 nm. The optimum conditions are with green light of 514–550 nm. The advantageous properties of these 3-furyl and 3-thienyl fulgides may be summarised as follows:

1. These compounds show slow photochemical reversal in some cases, allowing near non-destructive read-out at wavelengths *below* 600 nm.
2. They have good thermal stability.
3. They exhibit high conversions into the coloured forms.
4. Photochemical decay products do not interfere with the photochromic properties.

These photochromic compounds are therefore suitable for a wide variety of uses, including optical information storage and display systems but have the limitation that the coloured forms absorb only very weakly radiation above 600 nm so that they are not suitable for optical read/write/erase systems which use helium-neon lasers or laser diodes, which emit light at wavelengths longer than 600 nm.

SUMMARY OF THE INVENTION

It has now been discovered that a series of structurally similar compounds can be prepared, which are 3-pyrryl fulgides. These compounds are also photochromic and behave in a similar way to the fulgides described in the above U.S. patent, except that their photocoloured forms are deep blue, rather than red to purple so that they show maximum absorption in the visible region above 600 nm.

The photochromic 3-pyrryl fulgides of this invention are represented by formula (II) below:

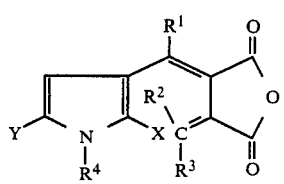

wherein:
$R^1$ represents an alkyl, aryl, or aralkyl group,
$R^2$ and $R^3$ independently represent an alkyl, aryl or aralkyl group or one of $R^2$ and $R^3$ represents hydrogen and the other an alkyl, aryl or aralkyl group or the group

represents an adamantylidene group,
X represents hydrogen or an alkyl, aryl or aralkyl group,
Y represents an alkyl or aralkyl group and
$R^4$ represents an alkyl, aralkyl or aryl group.

The invention includes the fulgimides corresponding to the fulgides of formula (II) above, i.e. corresponding succinimides in which the imide group may be substituted by an alkyl or aryl group.

Although the 3-furyl or 3-thienyl fulgides described in the above cited Heller patent include compounds in which Y is hydrogen, the present invention does not extend to the corresponding 3-pyrryl compounds in which Y is hydrogen. Contrary to what might be supposed on the basis of the prior art, if attempts are made to prepare 3-pyrryl fulgides in which Y is hydrogen, the compounds are found to be much more susceptible to photodegradation than when Y is an alkyl or aryl group, possibly because of photooxidation. Furthermore, compounds in which Y is hydrogen are extremely difficult to prepare, being obtainable only in very low yields (1 to 2%) and in the presence of black intractible oils from which they are difficult to separate.

A preferred range of 3-pyrryl fulgides and fulgimides in accordance with this invention are compounds of formula (II) in which:
$R^1$ represents an alkyl group, preferably a lower alkyl group having 1 to 5 carbon atoms, e.g. methyl, ethyl, propyl or butyl;
$R^2$ and $R^3$ are the same or different alkyl groups especially lower alkyl groups having 1 to 5 carbon atoms, including cycloalkyl groups such as cyclopropyl, $R^4$ is a lower alkyl having 1 to 5 carbon atoms, e.g. methyl, ethyl, propyl or butyl, phenyl or substituted phenyl, e.g. p-tolyl, and X and Y are a lower alkyl groups, e.g. one of those enumerated above, phenyl or a substituted phenyl group, e.g. an alkyl substituted phenyl group).

The new photochromic 3-pyrryl fulgides share all the advantageous characteristics of their oxygen and sulphur analogues. However, in addition they undergo photocolouration to deep blue rather than to red or purple, i.e. they show maximum absorption in the visible region *above* 600 nm. This means that in general they absorb at a wavelength which is 100 nm longer than their corresponding oxygen or sulphur analogues and many of the compounds of this invention absorb strongly *above* 700 nm, depending on the polarity of their solvent or the matrix. In common with the compounds described in the above Heller U.S. patent the 3-pyrryl fulgides are solvatochromic and show bathochromic shifts of the coloured forms with increasing polarity of the solvent medium.

Compounds of this invention may be prepared by a Stobbe condensation by condensing an appropriate ketone with a succinic acid ester in an analogous way to that described in the above Heller U.S. patent and in British Pat. No. 2002752, (which is particularly concerned with the adamantylidene fulgides). Reference may also be made to Chapter 1 of Vol. 6 of "Organic Reactions" published by Wiley, New York, 1951, pages 1 to 73. The 3-pyrryl fulgides of this invention may be prepared by a Stobbe condensation using a ketone of the following general formula as the starting material:

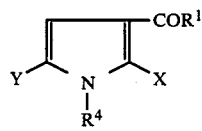

in which X, Y, $R^1$ and $R^4$ have the same significance as indicated above in connection with formula (II). The disclosure of these prior references is specifically incorporated herein for further details of preparations of the 3-pyrryl fulgides of this invention. The fulgimides may be prepared from their corresponding fulgides by any of the techniques described in U.S. Pat. No. 4,220,708.

Specific examples of the compounds of the invention are those of the formulae (II) and (IV) below:

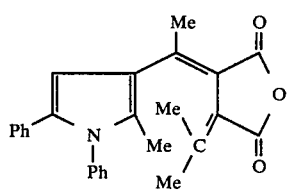 (III)

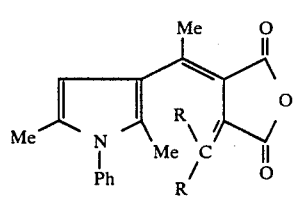 (IV)

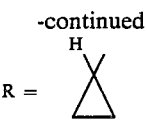

The compounds of formulae (III) and (IV) may thus be prepared, for example, by condensing a ketone of the formulae (V) or (VI), respectively

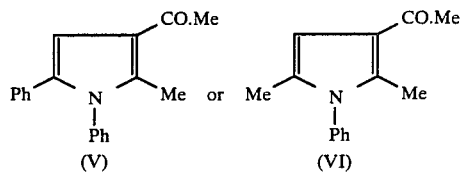

with an ester of a succinic acid derivative of the following formulae (VII)

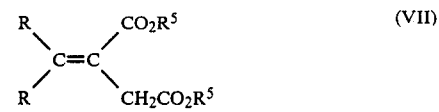 (VII)

wherein R is methyl or cyclopropyl and $R^5$ is the residue of an alcohol, by a Stobbe condensation, hydrolysing the half-ester so formed to form the di-acid, and then heating the resulting diacid with an acid chloride to give the product of formula (III) or (IV). Other compounds of formula (II) may be prepared by the same reaction using appropriate ketones and succinic acid ester derivatives. The Stobbe condensation may be carried out by refluxing the reactants in t-butanol containing potassium t-butoxide. The product of this stage is the half-ester, i.e. where one $R^5$ group is hydrogen. This is then converted into the di-acid by hydrolysis e.g. by boiling with ethanolic potassium hydroxide. The di-acid is then converted into its anhydride by a dehydration reaction comprising heating with an acid chloride. Preferably acetyl chloride is used for this purpose.

The photocoloured forms of the compounds of this invention have a broad intense long wavelength absorption band believed to be as a result of the presence of the nitrogen in the heterocyclic ring system.

The photocoloured forms of such compounds are thermally stable and resistant to fatigue. Thermal ring opening is believed to be prevented by steric hindrance between the groups represented by X and $R^3$ in formula (II) and a shift of X to a different position does not occur. It is this interaction and the stability of the substituent in the 2-position which is responsible for the thermal stability of these compounds. The colouring process takes place by subjecting the compounds to near ultraviolet radiation (e.g. 366 nm) and the photoreverse process takes place in the visible spectrum, the optimum conditions being with red light at 600-650 nm, e.g. by means of a helium neon laser.

The compounds of the invention exhibit the following properties:

1. They show slow photochemical reversal in some cases, allowing near non-destructive read-out at wavelengths *above* 600 nm;
2. They have good thermal stability;
3. They exhibit a high conversion into the coloured species;

4. The photochemical decay products do not interfere with the photochromic properties.

The compounds are suitable for a wide variety of uses. They may be used for information storage and display, including holographic recording. For details of the use of the compounds of this invention in data recording and similar applications, reference may be made to U.K. Patent Application No. 2,002,752, and U.S. Pat. No. 4,186,002, the disclosure of which is specifically incorporated herein.

The compounds of this invention may be incorporated within or coated onto a light transmissive support, e.g. a plastics film. When presented in such a form, the compounds should be protected from oxidation, e.g. by encapsulation or by inclusion of an oxygen scavenger in the plastics material.

The invention will be illustrated with reference to the following Examples in which parts are by weight unless otherwise indicated. The structural formulae of the compounds prepared in the Examples are given after the Examples, together with spectra of the compounds of Examples 2 and 4.

EXAMPLE 1

Preparation of (E)-α-(1,2,5-trimethyl-3-pyrryl)ethylidene(isopropylidene)succinic anhydride A mixture of 3-acetyl-1,2,5-trimethylpyrrole (16 parts) and diethyl isopropylidenesuccinate (22 parts) was added to potassium t-butoxide (12.5 parts) dissolved in t-butanol (400 parts by volume). The mixture was boiled. When the reaction was complete, t-butanol was removed and the residue was treated with water and extracted with toluene. The aqueous alkaline solution was acidified with hydrochloric acid and the liberated half-ester (13 parts) was hydrolysed by boiling with 10% ethanolic potassium hydroxide. The sparingly soluble potassium salt was removed by filtration. The potassium salt of the diacid was dissolved in water and the diacid liberated by the addition of hydrochloric acid.

The dried acid (1 part) with acetyl chloride (5 parts by volume) were allowed to stand at room temperature. Removal of excess acetyl chloride left a black oil which was purified by column chromatography on silica gel, using a 1:1 mixture of chloroform and light petroleum as eluant. The pale yellow photochromic fraction was separated and evaporated. The residue was crystallised from chloroform and petroleum, giving pale yellow crystals, m.p. 151° C., which on irradiation at 366 nm turn deep blue. The colour is reversed by white light.

EXAMPLE 2

Example 1 was repeated using 3-acetyl-2,5-dimethyl-1-phenyl-pyrrole (20 parts) in place of 3-acetyl-1,2,5-trimethylpyrrole. (E)-α-(2,5-dimethyl-1-phenyl-3-pyrryl)ethylidene(isopropylidene)succinic anhydride was obtained as yellow plates, m.p. 172° C., which, on irradiation at 366 nm, turn deep blue. The colour is reversed on exposure to white light.

EXAMPLE 3

Example 1 was repeated using 3-acetyl-2,5-dimethyl-1-p-tolyl-pyrrole (23 parts) in place of 3-acetyl-1,2,5-trimethylpyrrole. (E)-α-(2,5-dimethyl-1-p-tolyl-3-pyrryl)ethylidene(isopropylidene)succinic anhydride was obtained as yellow needles, m.p. 129° C., which, on irradiation at 366 nm, turn deep blue. The colour is reversed on exposure to white light.

EXAMPLE 4

Example 1 was repeated using 3-acetyl-1,5-diphenyl-2-methyl-pyrrole (26.5 parts) in place of 3-acetyl-1,2,5-trimethylpyrrole. (E)-α-(1,5-diphenyl-2-methyl-3-pyrryl)ethylidene(isopropylidene)succinic anhydride was obtained as yellow crystals, m.p. (to follow), which, on irradiation at 366 nm, turn deep blue. The colour is reversed on exposure to white light.

EXAMPLE 5

Example 2 was repeated using diethyl dicyclopropylmethylene-succinate (26.6 parts) in place of diethyl isopropylidene-succinate.

(E)-α-(2,5-dimethyl-1-phenyl-3-pyrryl)ethylidene(dicyclopropylmethylene)succinic anhydride was obtained as yellow plates, m.p. 145° C. which, on irradiation at 366 nm, turn deep blue. The colour is reversed by white light.

The accompanying spectra, marked FIGS. 1 to 4, illustrate the photochromic behaviour of the compounds of this invention.

FIG. 1 shows in full lines the absorption spectrum of the compound of Example 2 in its colourless state, while the broken line indicates the absorption spectrum of the cyclised coloured form, which has the structure shown in the right hand formula in FIG. 1. As can be seen the coloured form has a maximum absorption band at about 600 nm in the visible range and shows a reduced absorbance in the U.V. range compared with the colourless form.

FIG. 2 similarly shows the spectra of the colourless and coloured forms of the compound of Example 4 and it will be seen that the Example 4 compound behaves in a similar fashion.

Figure 1:
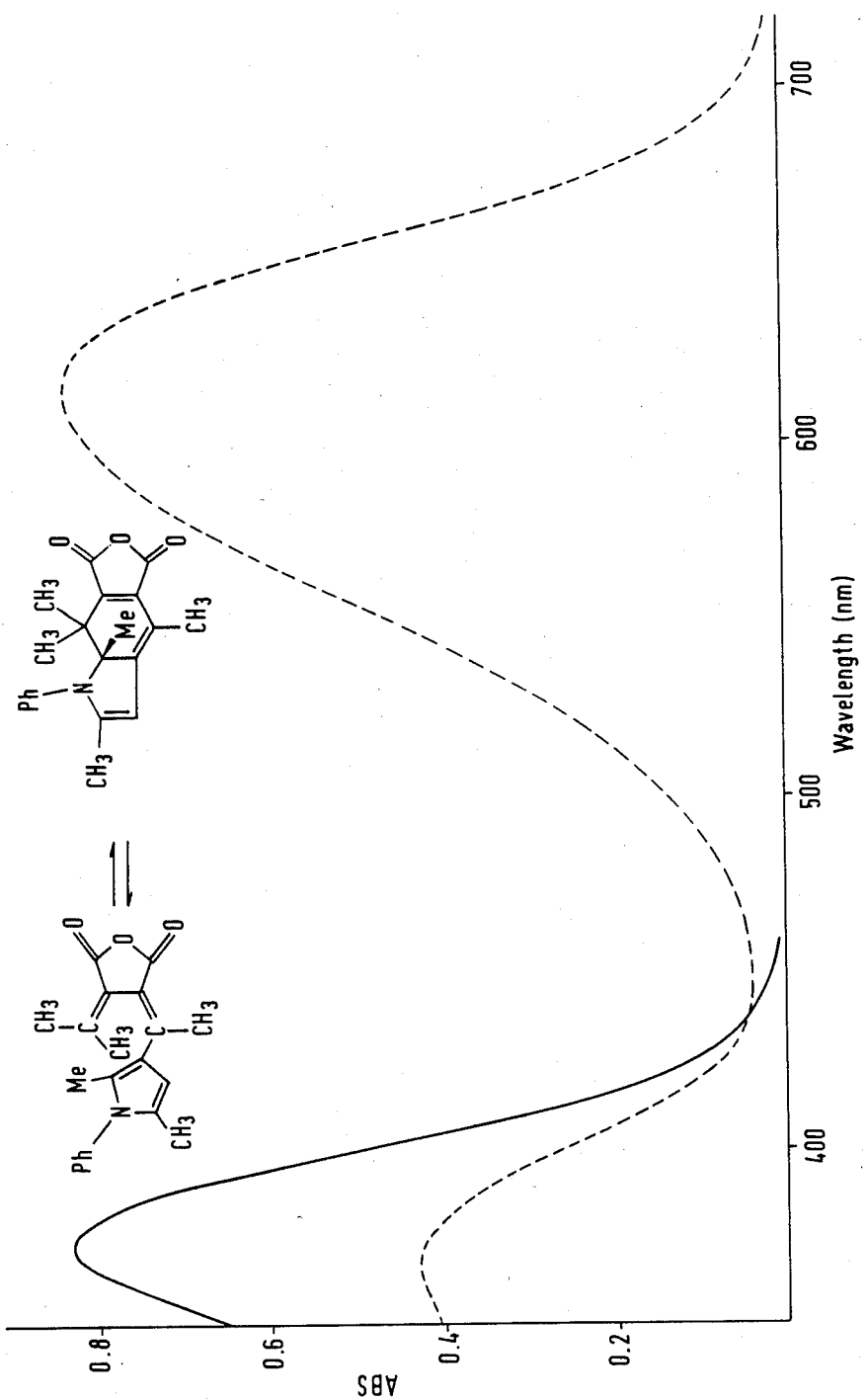
Figure 2:
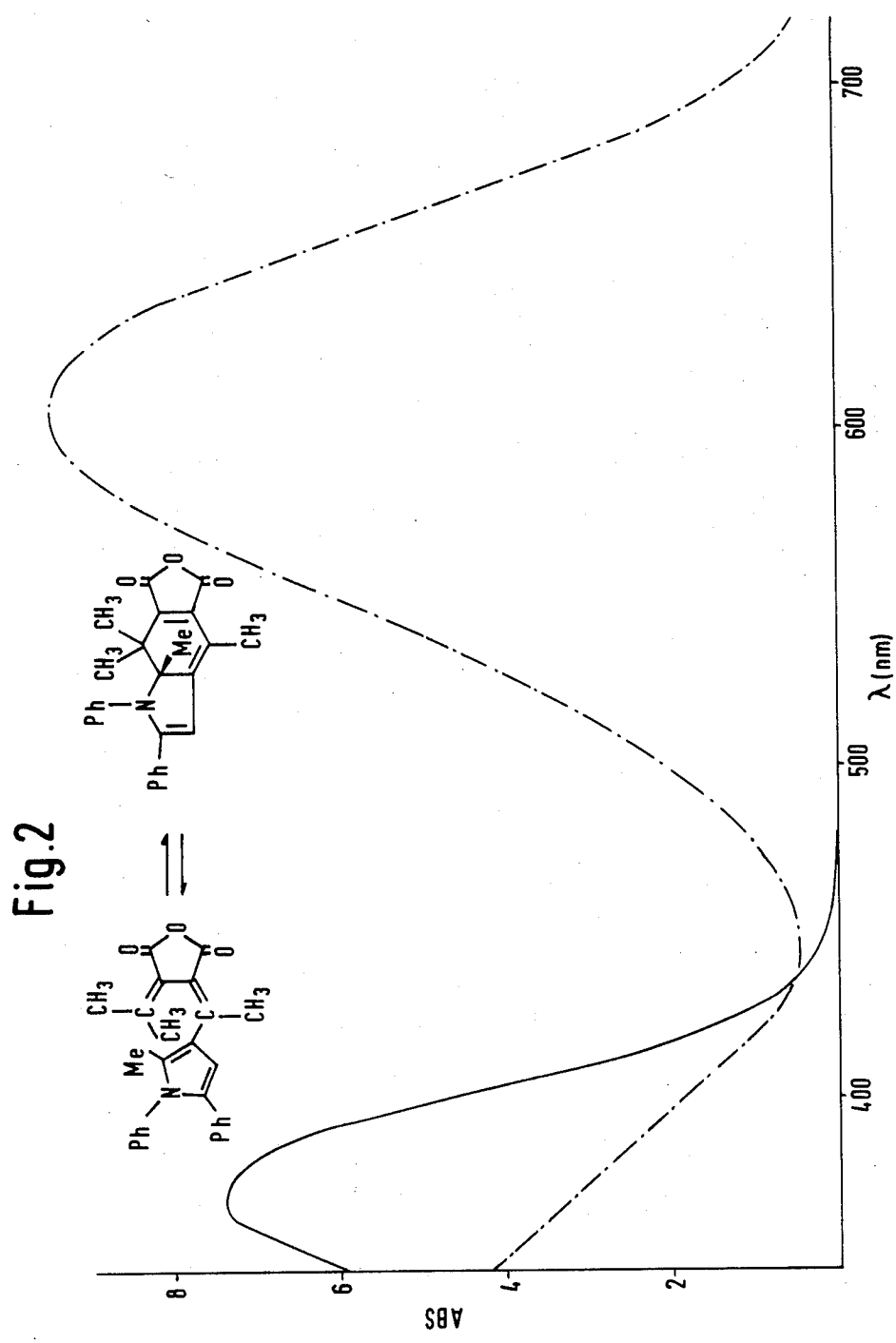
Figure 3:
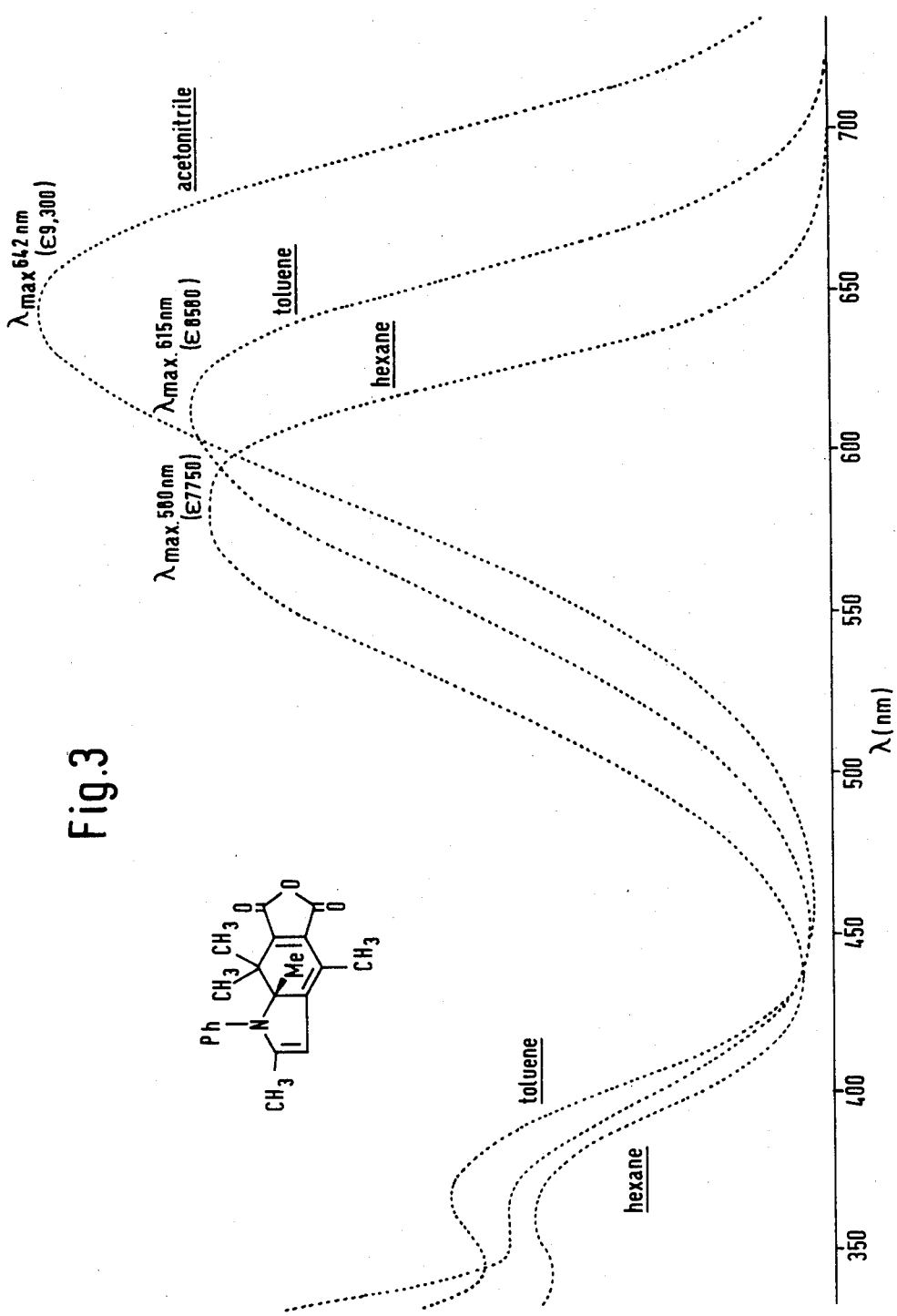
FIG. 3 shows the spectra of the compound of Example 2 in its coloured form in different designated solvents. This illustrates the solvatochromic behaviour of these compounds.
Figure 4:
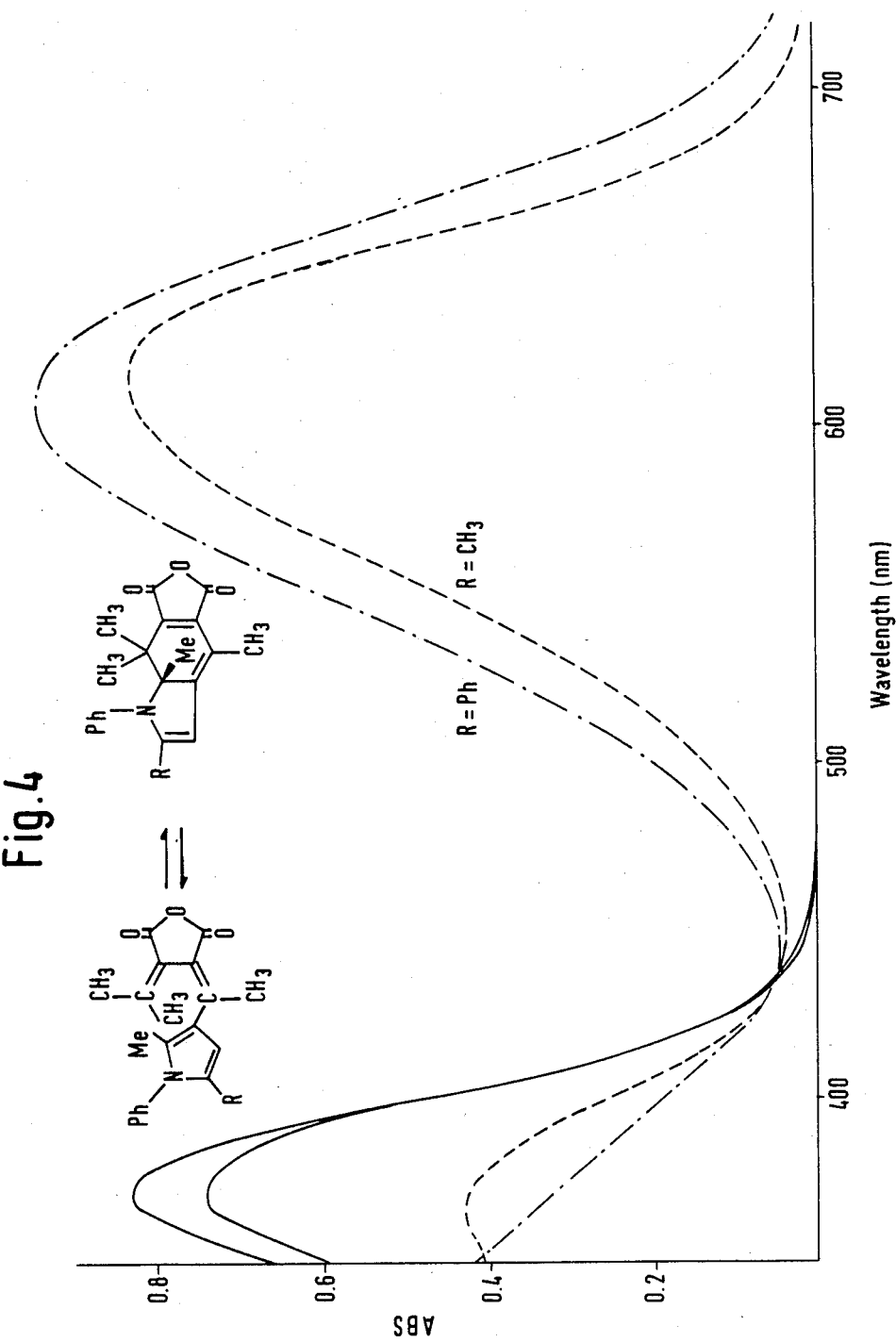
FIG. 4 is a plot of the spectra of FIGS. 1 and 2 on the same scale to show the effect on the spectra of different substituents in the 5-position.
Figure 5:
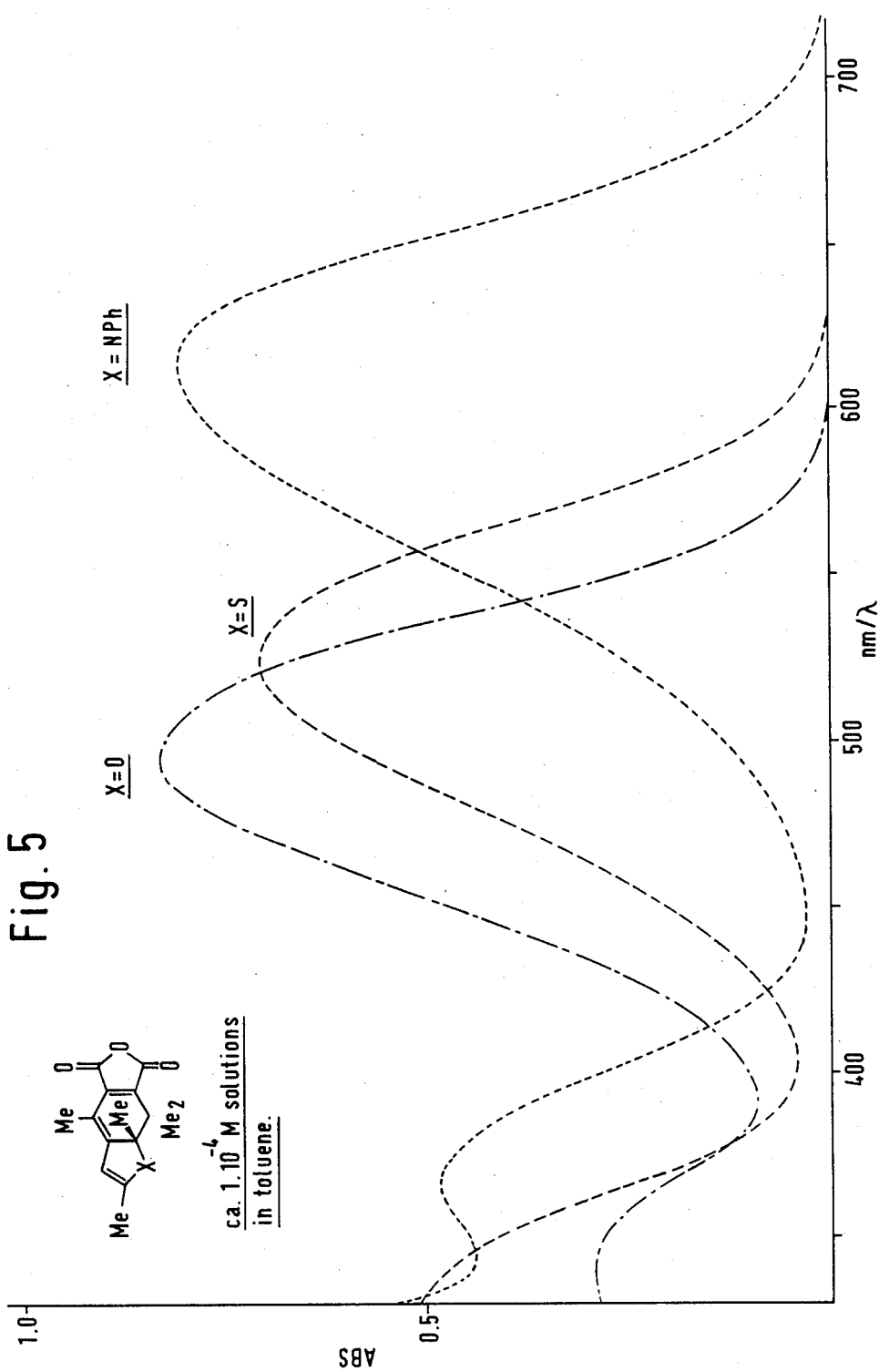

FIG. 5 shows the spectra of the compound of Example 2, and of the corresponding 3-furyl and 3-thienyl fulgides. This illustrates the marked shift of the absorption maximum towards the blue and of the visible region which arises in the case of the 3-pyrryl fulgides.

FIG. 6 shows the structural formulae and absorbance of the products produced in Examples 1–5.

What is claimed is:

1. A photochromic compound of the formula:

wherein
$R^1$ represents an alkyl, aryl or aralkyl group,
A represents oxygen or $>N-R^6$, in which $R^6$ is hydrogen, alkyl or aryl, R² and R³ independently represent an alkyl, aryl or aralkyl group or one of R² and R³ represents hydrogen and the other an alkyl, aryl or aralkyl group or the group

represents an adamantylidene group,
X represents hydrogen or an alkyl, aryl or aralkyl group,
Y represents an alkyl or aryl group and
R⁴ represents an alkyl, aralkyl or aryl group.

2. A compound according to claim 1 in which R¹ represents a lower alkyl group having 1 to 5 carbon atoms.

3. A compound according to claim 2 in which R² and R³ each independently represent lower alkyl groups having 1 to 5 carbon atoms or cycloalkyl groups having 3 to 5 carbon atoms.

4. A compound according to claim 2, in which R⁴ represents a lower alkyl group having 1 to 5 carbon atoms, phenyl, or a substituted phenyl group.

5. A 3-pyrryl fulgide having the formula:

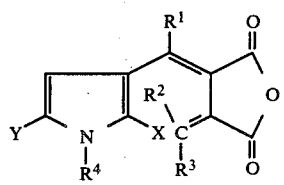

(II)

wherein
R¹ represents an alkyl, aryl or aralkyl group,
R² and R³ independently represent an alkyl, aryl or aralkyl group or one of R² and R³ represent hydrogen and the other an alkyl, aryl or aralkyl group or the group

represents an adamantylidene group,
X represents hydrogen or an alkyl, aryl or aralkyl group,
Y represents alkyl or aryl and
R⁴ represents alkyl, aralkyl or aryl.

6. A fulgide according to claim 5 in which R¹ represents a lower alkyl group having 1 to 5 carbon atoms.

7. A fulgide according to claim 6 in which R² and R³ are the same or different lower alkyl groups having 1 to 5 carbon atoms or cycloalkyl groups having 3 to 5 carbon atoms.

8. A fulgide according to claim 7 in which at least one of R² and R³ is a cycloalkyl group.

9. A fulgide according to claim 6 in which R⁴ is a lower alkyl group having 1 to 5 carbon atoms, phenyl or a substituted phenyl group.

10. A photochromic image or data recording or display device which comprises a substrate having a photochromic compound as claimed in claim 5, in a coating or layer on said substrate.

11. A device according to claim 10 in which the photochromic compound is encapsulated in a light transmissive layer which is non-permeable to oxygen.

* * * * *